United States Patent [19]

Rutecki et al.

[11] Patent Number: 5,330,515
[45] Date of Patent: Jul. 19, 1994

[54] TREATMENT OF PAIN BY VAGAL AFFERENT STIMULATION

[75] Inventors: Paul Rutecki, Houston; Joachim F. Wernicke, League City; Reese S. Terry, Jr., Houston, all of Tex.

[73] Assignee: Cyberonics, Inc.

[21] Appl. No.: 900,007

[22] Filed: Jun. 17, 1992

[51] Int. Cl.⁵ .................................. A61N 1/05
[52] U.S. Cl. ......................................... 607/46
[58] Field of Search ............... 128/419 C, 419 R, 421, 128/422

[56] References Cited

U.S. PATENT DOCUMENTS

| | | | |
|---|---|---|---|
| 3,796,221 | 3/1974 | Hagfors | 128/419 C |
| 4,865,048 | 9/1989 | Eckerson | 128/421 |
| 4,867,164 | 9/1989 | Zabara | 128/421 |
| 5,188,104 | 2/1993 | Wernicke et al. | 128/419 C |

*Primary Examiner*—William E. Kamm
*Assistant Examiner*—Scott M. Getzow
*Attorney, Agent, or Firm*—O'Connor, Cavanagh

[57] ABSTRACT

Method and apparatus for treating severe chronic, persistent or recurring neuropathic or psychogenic pain, or pain which is nociceptive if the patient is suffering from terminal disease, by selectively applying a pulse waveform to a lead/electrode implanted on the patient's cervical vagus nerve or other site preferably above the location of the pain to stimulate afferent fibers for activating a descending anti-nociceptive pathway and thereby blocking incoming pain signals. The pulse waveform has programmable pulse width, current level and frequency, and pulse sequence on and off time durations. The programmed pulse sequences are applied to the implanted electrode either on a continuous basis, or only during the period the patient is normally awake, or is initiated by the patient or automatically in response to the onset of pain. A method for use in advancing relief and control of pain includes providing the lead/electrode assembly to be implanted and the generator for the programmable pulse sequences, incorporating a connector on the generator to accommodate the lead, restricting the ranges of programmable values of the pulse sequences to values which in combination will stimulate the small afferent fibers of the vagus nerve to activate a descending anti-nociceptive pathway, and adapting the generator for physician selection of manner of control of commencement and cessation of the pulse sequences.

16 Claims, 3 Drawing Sheets

TREATMENT OF PAIN BY VAGAL AFFERENT STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient, and more particularly to techniques for treating painful syndromes in patients by selective electrical stimulation of vagus nerve afferent fiber activity with an implanted neurostimulating device.

The most commonly experienced form of pain may be defined as the effect of a stimulus on nerve endings, which results in the transmission of impulses to the cerebrum. This important somatic sensation and normal function of pain, referred to as nociception or nociceptive pain, informs the organism of impending tissue damage. Somatic and visceral free nerve endings, termed nociceptors, initially process such pain signals. A pathway for nociceptive pain exists within the central nervous system (CNS) through three orders of neurons, the basic excitable cell units of the nerve tissue in the nervous system. Each neuron transmits impulse information regarding the stimulus on the nerve endings along portions of the pathway.

Certain types of pain, however, including neuropathic pain and psychogenic pain, may develop without actual impending tissue damage. The term "neuropathic" relates to any disease of the nervous system and implies an underlying disease process or injury, in contrast, for example, to "neurogenic" which refers to commencing from or being caused by the nervous system. Neuropathic pain typically occurs following injury to elements of the nervous system involved in nociception, such as peripheral nerve injury, in which the lesions deafferent (i.e., remove the afferent or incoming signal fiber functions of) the nociceptive pathway, and the resultant pain is sometimes called deafferentation pain. Deafferentation is the state of loss of afferent input as occurs following peripheral nerve injury or peripheral neuropathies.

The nociceptive pathway exists for protection of the organism (such as the pain experienced in response to a burn), being inactive unless there is danger to the organism, and begins with peripheral receptors being activated. The signal travels up the peripheral nerve and into the spinal cord where synapses are made on second order neurons, which then transmit the pain signal up the spinal cord in the spinothalamic tract ending in the thalamus. Most authorities believe that pain is recognized or perceived in the thalamus. The ventrolateral and ventromedial thalamic nuclei project to the cortex where the pain is then processed with regard to localization and other integrative characteristics.

On the other hand, the neuropathic or psychogenic pain pathways are not associated with immediate action to prevent injury. The pain experienced following amputation of a limb, for example, is neuropathic—there is no danger of injury to the missing limb. Psychogenic pain is a chronic condition of pain without definite organic pathology.

By way of further exploration of the anatomy or mechanism of pain, the nerves themselves are composed of thousands of fibers of different sizes, classified by groups A, B and C. A and B fibers include axons having a myelin sheath, i.e., are myelinated, whereas the C fiber axons are unmyelinated. Axons of the A group are divided into subgroups alpha ($\alpha$), beta ($\beta$), gamma ($\gamma$) and delta ($\delta$). The pain signals originate from peripheral neural receptors, i.e., sensory nerve endings responsive to stimulation, usually from free nerve endings in the skin or the organs. When activated, a graded receptor potential is generated which causes the axon to fire action potentials. These are electrical impulses which self-propagate in a series of polarizations and depolarizations transmitted down the axon. It is not clear whether specific pain fibers exist or the sensation of pain lies in the recognition of a pattern of impulses, but in any case the pain sensations are usually carried by small diameter A$\delta$ fibers or C fibers. The receptor potential varies in amplitude initially and with time and may dissipate rapidly despite a continuing stimulus, with a consequent reduction in the firing frequency in the nerve fiber.

The cell body of a sensory neuron lies in the dorsal (posterior) root ganglion. The central process of the dorsal root ganglion cells enters the dorsal root and ascends and descends via the pathway of axons known as the tract of Lissauer up to 3 or 4 dermatome levels. Synapses for transmission of impulses between these first order neurons and second order neurons are made in the dorsal horn of the spinal cord, especially the substantia gelatinosa. The second order neurons then send their processes to the contralateral spinothalamic tract in the ventral (anterior) lateral aspect of the spinal cord. In an ascending pathway, the axons travel in the spinothalamic tract upward to the thalamus where they synapse on third order neurons in the ventral posterolateral nucleus of the thalamus (or posteromedial, for sensation from the face). From there, projections (processes) are formed with a variety of cortical and subcortical structures.

There is also a descending pathway which inhibits the incoming pain signals, and is therefore important in the body's own, i.e., endogenous, control of pain. This system includes the periaqueductal grey, the dorsal raphe nuclei, locus ceruleus, and nuclei of the medullary reticular formation. The nuclei send descending axons in the dorsolateral funiculus and synapse in the dorsal horn of the spinal cord. Spontaneous activation of these pathways, some of which involve activation of the endogenous opiate system, tends to suppress pain transmission.

In addition to these central connections, it has been theorized that other projections from the periphery may help to gate pain. The gate theory of pain, for example, postulates that the large diameter sensory fibers inhibit incoming small diameter fiber signals, e.g., that pain transmission is inhibited with the activation of large diameter A afferents which are activated by vibration. This is the reason one shakes his or her hand when it is burned. It is also the basis for the transcutaneous electrical nerve stimulation (TENS) analgesia, a non-invasive procedure in which electrical impulses from an external stimulator unit are applied through electrodes placed on the skin to reduce the transmission of pain signals to the brain.

Some pain syndromes are associated with overactivity of the sympathetic nervous system which occurs following peripheral nerve injury. The resulting pain and sympathetic activity is termed causalgia. Some evidence exists that norepinephrine, one of the transmitters of the sympathetic system, may excite nociceptive fibers and lead to this abnormal pain. Conversely, it may be that aberrant nerve transmission results in activation of sympathetic afferents and leads to overactivity.

The sensation of pain is subjective. The clinical reaction differs from patient to patient, and the patient's interpretation of the sensation and its potential sources may lead to apprehension and distress that exceeds or exacerbates the pain itself. It has been theorized that concentrations of excitatory and inhibitory neurotransmitters in the spinal cord and the brain may vary from individual to individual in response to different stimuli, and may be part of the basis for differences in the tolerance for pain among individuals, and even in the same individual over time. In any event, the tolerance for or threshold of pain is a dynamic process which depends on the organism's state. For example, minimal pain may be experienced in certain injuries suffered by soldiers in battle.

Diagnosis by the physician of the site and nature of the underlying pathology of pain depends almost entirely on historical information provided by the patient regarding its location, the extent that it tends to radiate, its intensity, whether it is continual or recurring, the conditions or medications which tend to reduce or increase its severity, and various other factors. This is complicated by the fact that different patients may describe pain and its apparent sources in vastly different ways, or be virtually unable to describe it adequately as to specific site or nature. The prescription of proper treatment, of course, depends on an understanding of the underlying organic basis of the pain, and is particularly difficult with those patients who experience chronic pain syndromes.

Persistent pain may, despite careful examination and investigation, lack apparent anatomical cause or be of uncertain nature. The patient may be experiencing post herpetic pain, or pain resulting from a central engram. In post-herpetic neuralgia, the sensory ganglion associated with the dermatome from which the pain is referred may be destroyed and yet the pain persists. The theory is that other areas of the nervous system are involved in the generation of pain. Chronic pain seems to burn in a pathway or engram which, when activated, reproduces the pain even in the absence of sensation to touch or pin prick in the area in which the pain seems to occur.

Common complaints include existence of spinal pain, usually in the cervical or lower spine, headache, facial pain, neck pain, and pain in the extremities. Chronic pain which lacks pathological basis is psychogenic, and may be symptomatic of patients suffering from tension, anxiety, depression, hysteria, hypochondria, or simply malingering. Persistent or recurring pain may instead be neuropathic, attributable to a carefully diagnosed condition such as arthritis, peripheral nerve pain such as causalgia, or peripheral neuropathy, for which treatment by analgesics and local anesthetic injections is often prescribed. Hyperpathia and hyperalgesia patients suffer excessive painful reaction to what may be characterized as normal pain sensations in most individuals.

An inability to diagnose an underlying pathological cause does not make the pain less real, and, for many chronic pain sufferers, it may be debilitating or disabling. The psychological effect of chronic pain is a complicating factor. With time, persistent pain may tend to take on greater, rather than less significance as in the case of most sensory stimuli. Fear associated with constant or intermittent pain may raise the specter of life-threatening disease, with consequent anxiety, irritability, insomnia, and depression. Conversely, individuals suffering from anxiety, depression or other psychological disorder may experience resultant pain syndromes.

Drug therapy is the principal form of treatment for pain today, including widespread use of analgesics, corticosteroids, antidepressants, topical anesthetics and local anesthetic injections. In an acute setting, such as after surgery, narcotics and anti-inflammatory drugs are used. For chronic pain, narcotics are generally avoided as a prescribed treatment, in favor of anti-inflammatory drugs. Other drug therapies include tricyclic antidepressants which help to activate some of the descending pathways that provide analgesia. In some cases, local or systemic administration of anesthetic agents are used. For patients with intractable pain, especially cancer patients, opiates have been delivered to the cerebrospinal fluid at programmed times by means of external drug pumps.

As noted above, TENS analgesia has been useful in controlling pain. Such treatment is most useful for pain following peripheral nerve injury (deafferentation) or back pain which is chronic and refractory to surgical therapy or in cases where surgery is not indicated. Other therapies that involve central stimulation include dorsal column stimulation and CNS stimulation. Dorsal column stimulation requires implantation of electrodes in the dorsal column of the spinal cord where, it is presumed, activation of these fibers helps to suppress incoming pain signals. The dorsal columns originate from the large (AB) fibers, the same fibers that are activated by TENS units. CNS stimulation usually involves the periaqueductal grey in the midbrain. Stimulation of the periaqueductal grey activates descending inhibitory pathways, and analgesia is blocked by opiate antagonists.

In rare situations, ablative procedures have been used to control chronic pain by interrupting the afferent pain pathways. The peripheral root may be cut to block incoming fibers. The ventral lateral aspect of the cord that contains spinothalamic fibers may be lesioned. In some cases, sectioning of the cingulate gyrus may aid in controlling pain. In cases where the pain returns, lesions may continue to be made higher up the nervous system axis. The belief is that a pain engram or memory is formed and distributed in multiple CNS sites.

In causalgia, a block of the sympathetic ganglion may reduce pain. In these cases, sympathectomy may be an effective treatment. Persons suffering from persistent and/or severe pain have also sought relief through therapies which may loosely be characterized as alternative medicine, such as acupuncture and hypnosis.

As will be discussed in greater detail below, the present invention provides improvements in therapy for alleviating chronic or persistent pain, particularly neuropathic and psychogenic pain, by electrical stimulation of the afferent fibers of the vagus nerve to modulate the electrical activity of the nerve, primarily to activate the descending anti-nociceptive pathway, to inhibit the sensation of pain.

For the moment, however, by way of further background it is noteworthy that the vagus nerve has approximately 100,000 fibers of the A, B and C classifications. Each carries electrical signal information to and from the brain. The myelinated A and B fibers are typically larger, have faster electrical conduction and much lower electrical stimulation thresholds than the unmyelinated C fibers, and exhibit a particular strength-duration curve in response to a specific width and amplitude of stimulation pulse. A and B fibers are stimulated with relatively narrow pulse widths, from 50 to 200 microseconds ($\mu s$), for example. A fibers exhibit slightly faster electrical conductivities than B fibers, and slightly lower electrical stimulation thresholds. C fibers require wider pulse widths (e.g., 300–1000 $\mu s$) and higher amplitudes for activation. Although the A and B fibers may be selectively stimulated without also stimulating the C fibers, the magnitude and width of the pulse required for stimulating the C fibers would also activate A and B fibers.

The vagus nerve is composed of somatic and visceral afferents (i.e., inward conducting nerve fibers which convey impulses toward a nerve center such as the brain or spinal cord) and efferents (i.e., outward conducting nerve fibers which convey impulses to an effector to stimulate it and produce activity). The vast majority of vagal nerve fibers are C fibers, and a majority are visceral afferents having cell bodies lying in masses or ganglia in the skull. The central projections terminate largely in the nucleus of the solitary tract which sends fibers to various regions of the brain (e.g., the hypothalamus, thalamus, and amygdala); others continue to the roedial reticular formation of the medulla, the cerebellum, the nucleus cuneatus and other regions. Afferents activate both ascending and descending pathways.

In an article in the Journal of Neurophysiology (Vol. 50, No. 4, October 1983, at p. 926), Ammons et al. reported that left thoracic vagal nerve (LTV) stimulation depressed the background activity of 61% of the spinothalamic (ST) neurons studied in the upper thoracic cord of a study group of anesthetized monkeys. It was found that stimulation of the vagus below the heart was ineffective in ten of the thirty-two ST cells. It was concluded that LTV stimulation alters activity of ST neurons in the upper thoracic spinal cord, and that inhibition of ST cell activity could be attributed to stimulation of cardiopulmonary vagal afferent fibers coursing to the brain stem, which then appeared to activate descending inhibitory spinal pathways.

Ren et al. reported in the Vol. 64, No. 4, October 1990 issue of the Journal of Neurophysiology, on p. 1098, that vagal afferent stimulation appeared to raise the nociceptive threshold in a group of anesthetized paralyzed rats subjected to noxious thermal stimulation. The results were felt to confirm the association between vagal afferent and nociceptive systems. Other investigators have found an anti-nociceptive effect of vagal afferent stimulation by observation of the response of the tail-flick reflex in rat studies (e.g., Randich et al. in Brain Research, 445 (1988) at p. 68; Ren et al., Brain Research, 446 (1988) at p. 285; and Maixner et al., Brain Research, 298 (1984) at p. 374). This analgesic effect could be blocked by lesioning of brain stem structures important in inhibiting incoming pain signals (e.g., locus ceruleus, nucleus raphe magnus, and nucleus of the solitary tract). The anti-nociceptive effect was found to be sensitive to naloxone, an opiate antagonist. Stimulation of the nucleus of the solitary tract, which is the destination of many of the vagal afferents, also inhibits nociceptive reflexes.

SUMMARY OF THE INVENTION

The present invention is principally concerned with the treatment of neuropathic and psychogenic pain by blocking the sensation of pain through selective stimulation of the afferents of the vagus nerve to activate a descending anti-nociceptive pathway of the nerve tract. In general, however, such treatment would not be recommended in the case of true nociceptive pain, precisely because of the capability of the treatment to mask the early and ongoing warning signs and signals of potentially serious disease or disorder. For example, patients with angina need to know if they are experiencing ischemia so that they do not have a myocardial infarction. In effect, the angina informs the patient to slow down or take a nitroglycerine. Nevertheless, the blocking of nociception would be an appropriate strategy to afford pain relief in the specific case of patients with terminal disease, either as a substitute for or an adjunct to opiate analgesia.

Activation of the descending anti-nociceptive pathway by stimulation of vagal afferents is, in many instances, an appropriate strategy for treatment of chronic pain of neuropathic or psychogenic origin, especially pain which is intractable to drug therapy.

Selective stimulation of the vagal afferents for treating and controlling pain according to the invention is performed using a neurostimulator, which is preferably but not necessarily implantable in the patient. The therapy is delivered from a pulse generator of the neurostimulator to a nerve electrode array implanted on the patient's vagus nerve to appropriately modulate the electrical activity of the nerve. The neurostimulator is programmed by the attending physician to provide the desired therapeutic modality for that purpose.

Selection among various strategies for vagal modulation in the treatment of pain depends on a number of factors. These include (i) a consideration of which of the nerve fibers are to be subjected to the stimulation; (ii) whether some type of physiologic signal is generated that can be detected and employed to trigger the stimulation; and/or (iii) whether a "carryover" or refractory period occurs following stimulation in which the benefit of the stimulation is maintained. Though not all of the factors which may need to be considered for determining the stimulation strategy for the therapy, nor necessarily listed in order of importance, these are indicative of considerations which may apply in a specific case.

In the treatment, the invention uses different signal parameters and threshold curves to activate the various fibers of the patient's vagus nerve for selective modulation of the electrical activity thereof. By appropriately setting pulse width and amplitude of the electrical signal to be delivered by the neurostimulator to the patient's vagus nerve, the nerve fibers can be selectively stimulated, such as A and not B and C; or A and B, but not C; or A, B and C. Although desensitizing the A and B fibers while stimulating the C afferent fibers appears to be appropriate for activation of the descending pathway to inhibit pain, it is not completely clear which of the afferent fibers are most important for that purpose. However, most of the vagus nerve comprises small C fibers, and while some stimulation of A and B fibers will take place as the C fibers are being stimulated with the desired effect, the effects of stimulating the larger fibers are likely to be minimal with some activation of motor and autonomic efferents.

Although the specific location of the implanted nerve electrode for purposes of the vagal stimulation is not critical to the effectiveness of the therapy, it is preferable that the stimulation site be above the point where the pain sensation is most pronounced to the patient. For example, stimulation of the vagus nerve in the abdominal region is likely to be less effective for treatment of arm pain than vagal stimulation in the neck region. There are exceptions, however, such as an indication from animal studies that cervical stimulation is effective in inhibiting lumbar dorsal horn neurons.

The preferred stimulation parameters are, in general, long pulse widths (e.g., up to about 2 milliseconds (ms)), at frequencies in the range from about 20 to about 40 hertz (Hz), and for durations in the range of seconds. Such a stimulation paradigm or regime is highly likely to excite and activate the small fiber afferents of the vagus nerve, with the desired effect of activating a descending anti-nociceptive pathway. It is anticipated that a threshold effect occurs with intensity of the pulses, in which the initial stimulation enhances dorsal root activity, for example, in the first one to two seconds and then results in suppression of firing. It is not clear whether a carryover effect occurs following stimulation.

Preferably, the neurostimulator is programmed to be activated automatically and periodically for predetermined intervals continuously throughout each 24-hour day. Alternatively, in cases where the intensity of the pain is not sufficiently severe to interfere with or interrupt patient sleep, the automatic periodic activation may be set to occur only during the approximate normal waking hours according to the circadian cycle of the patient. The stimulation strategy may instead or additionally be implemented manually by patient activation of the device upon sensing pain.

Broadly, then, the present invention is directed to apparatus and methods which employ a neurostimulator device, preferably implantable, for treating neuropathic or psychogenic pain through vagal stimulation therapy. The stimulation is intended to excite primarily the small C afferent fibers of the vagus nerve and thereby activate a descending pain pathway to inhibit or block the chronic or persistent pain otherwise experienced by the patient. The preferred site for the vagal stimulation is on the cervical vagus nerve, or at least at a point above the location of the pain felt by the patient, where the relative term "above" is used in this specification and the appended claims in a sense as though the patient were always upright even if, for example, actually supine.

A principal object of the invention is to employ vagal stimulation for blocking chronic neuropathic (deafferentation) pain and psychogenic pain. The invention is also useful in blocking nociceptive pain, but should be limited to those situations where the patient requiring pain relief has a terminal disease.

The pain suppression provided by the invention is to be distinguished from the extra-physiologic electrical stimulation of the vagus nerve for treatment of epilepsy and various forms of involuntary movement disorders disclosed in U.S. Pat. No. 4,702,254 to J. Zabara. In the disclosure of that patent, an implantable neurocybernetic prosthesis (NCP) utilizes spectral discrimination by tuning the external current of the NCP generator to the electrochemical properties of a group of inhibitory nerves that affect the reticular system of the brain, for alleviating or preventing epileptic seizures, characterized by abnormal neural discharge patterns of the brain. These nerves are selectively activated directly or indirectly by tuning the NCP to augment states of brain neural discharge to control convulsions or seizures. The spectral discrimination analysis dictates that certain electrical parameters of the NCP pulse generator be selected based on the electrochemical properties of the nerves desired to be activated.

The invention is also to be distinguished from the pain suppression performed by the prior art TENS and dorsal column stimulation techniques. Vagal stimulation performed according to the invention is stimulation of the nerve itself, in contrast to the activation of receptors by TENS units. Dorsal column stimulation is also at the cord level, and, like TENS therapy, is thought to work in accordance with the gate theory of pain described earlier herein. In fact, the pain associated with many neuropathies may result from loss of large fiber function and consequent inability of the large fiber sensory pathways to inhibit the incoming pain signals from small diameter pain fibers. With vagal stimulation, it does not appear to be an activation of somatic large fiber sensory nerves, but rather, an activation of brain stem centers which in turn activate a descending pathway to inhibit incoming pain signals. Thus, vagal stimulation is more akin to brain stem stimulation for pain control, but is much less invasive.

Accordingly, it is another important object of the invention to provide improved techniques for suppression of pain in appropriate cases by selective stimulation of the patient's vagus nerve to activate a descending pathway which inhibits incoming pain signals.

A further object is to modulate the electrical activity of the vagus nerve of a patient by selectively applying a predetermined electrical stimulus to the nerve as a technique for blocking afferent pain signals along a pain signal pathway to the brain. A related object is to perform the modulation by applying the electrical stimulus to the vagus nerve at a site above the locality of the pain, to enhance the blocking of incoming pain signals from that locality.

Yet another object of the invention is to provide a method for use in advancing the relief and control of pain, by providing an electrical lead with an electrode assembly adapted for implantation on a patient's vagus nerve, providing a programmable stimulus generator for generating electrical stimuli in the form of sequences of electrical pulses with selectively variable parameters including pulse width, amplitude and frequency and sequence duration and intervals, for application to the implanted lead/electrode assembly via a connector on the stimulus generator, restricting the ranges of programmability of the selectively variable parameters of the electrical pulse sequences generated by the stimulus generator to values which in combination will cause activation of a descending pain pathway activated by the vagus nerve and thereby inhibit afferent pain signals when the electrical stimuli are applied to the nerve via the lead/electrode assembly, adapting the stimulus generator for physician selection of the control of commencement and cessation of the electrical stimuli to the lead/electrode assembly, and supplying the stimulus generator and lead/electrode assembly for the relief and control of pain in sufferers from chronic pain.

Still another object of the invention is to provide the stimulus generator with one or more controls for selective activation of the stimulus generator to cause the electrical stimuli to be applied to the implanted lead- /electrode assembly. A related object is to permit one of the controls to be operated manually for patient activation of the stimulus generator, and/or automatically for activation of the stimulus generator upon detection of a physical reaction by the patient to the onset of pain, and/or continuously for ongoing or periodic delivery of electrical stimuli by the stimulus generator to the implanted lead/electrode assembly.

BRIEF DESCRIPTION OF THE DRAWINGS

The above and still further objects, aspects, features and attendant advantages of the present invention will be better understood from a consideration of the following detailed description of a presently preferred embodiment and method thereof, taken in conjunction with the accompanying drawings, in which.

DESCRIPTION OF THE PRESENTLY EMBODIMENT AND METHOD

Figure 1:
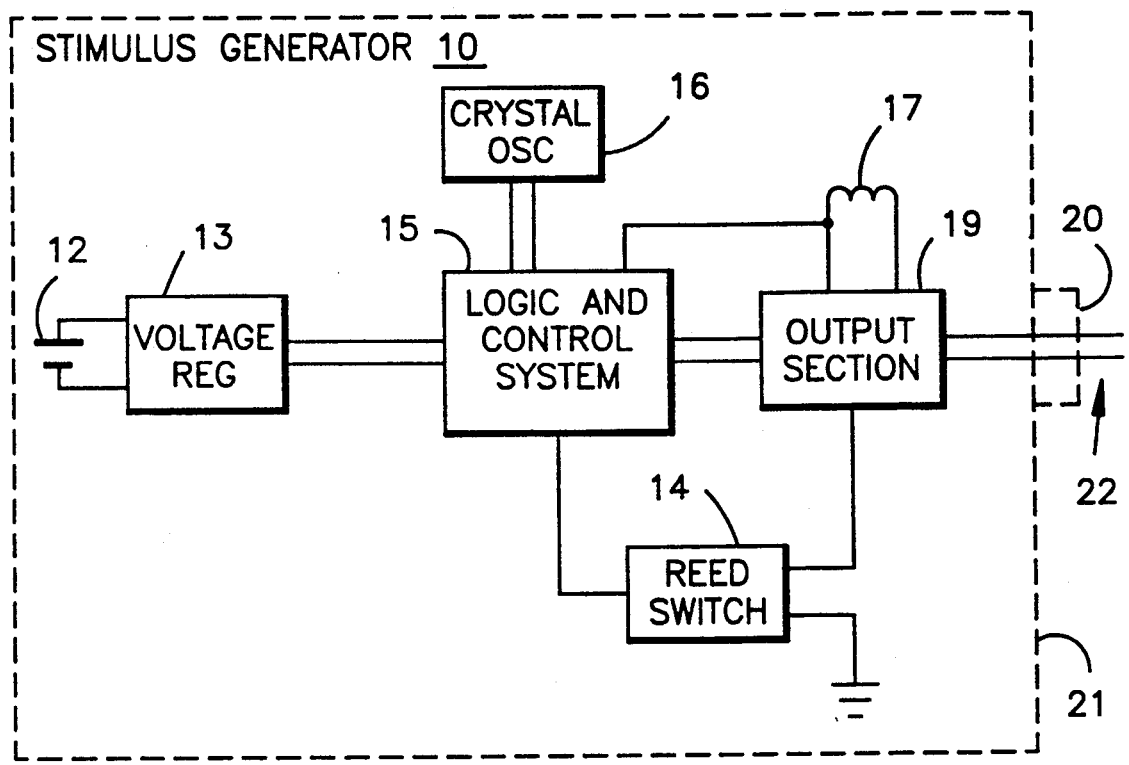
FIG. 1 is a simplified block diagram of an implantable neurostimulator electronics package (stimulus generator) for use (with appropriate parameter settings and ranges) in treating various pain syndromes according to the present invention.
Figure 3:
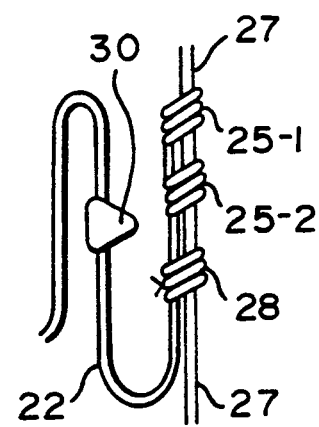
FIG. 3 is a more detailed fragmentary illustration of the nerve electrode as implanted for modulating the electrical activity of the vagus nerve.

Preferably, the electrical stimulus generator of a neurostimulator used for purposes of the present invention is the embodiment disclosed in copending U.S. patent application Ser. No. 07/434,985, now U.S. Pat. No. 5,154,172 issued Oct. 13, 1992 (the "'172 patent") assigned to the same assignee as the instant application, with such modifications and additions as are required by the description herein. The specification of the '985 application is incorporated herein in its entirety by reference, but certain portions of it are summarized in this application for the sake of convenience to the reader. Referring now to the drawings, a block diagram of the basic components of the stimulus (e.g., pulse) generator of a neurostimulator and their interrelationship is illustrated in FIG. 1. Further details of an exemplary location of an implantable version of the device and the associated lead/electrode system are shown in FIGS. 2 and 3.

The neurostimulator utilizes a conventional microprocessor and other standard electrical and electronic components, and in the case of an implanted device, communicates with a programmer and/or monitor located external to the patient's body by asynchronous serial communication for controlling or indicating states of the device. The neurostimulator also includes means for conserving energy, which is important in any battery operated device to be implanted for medical treatment of a disorder, and means for providing various safety functions such as preventing accidental reset of the device.

Figure 2:
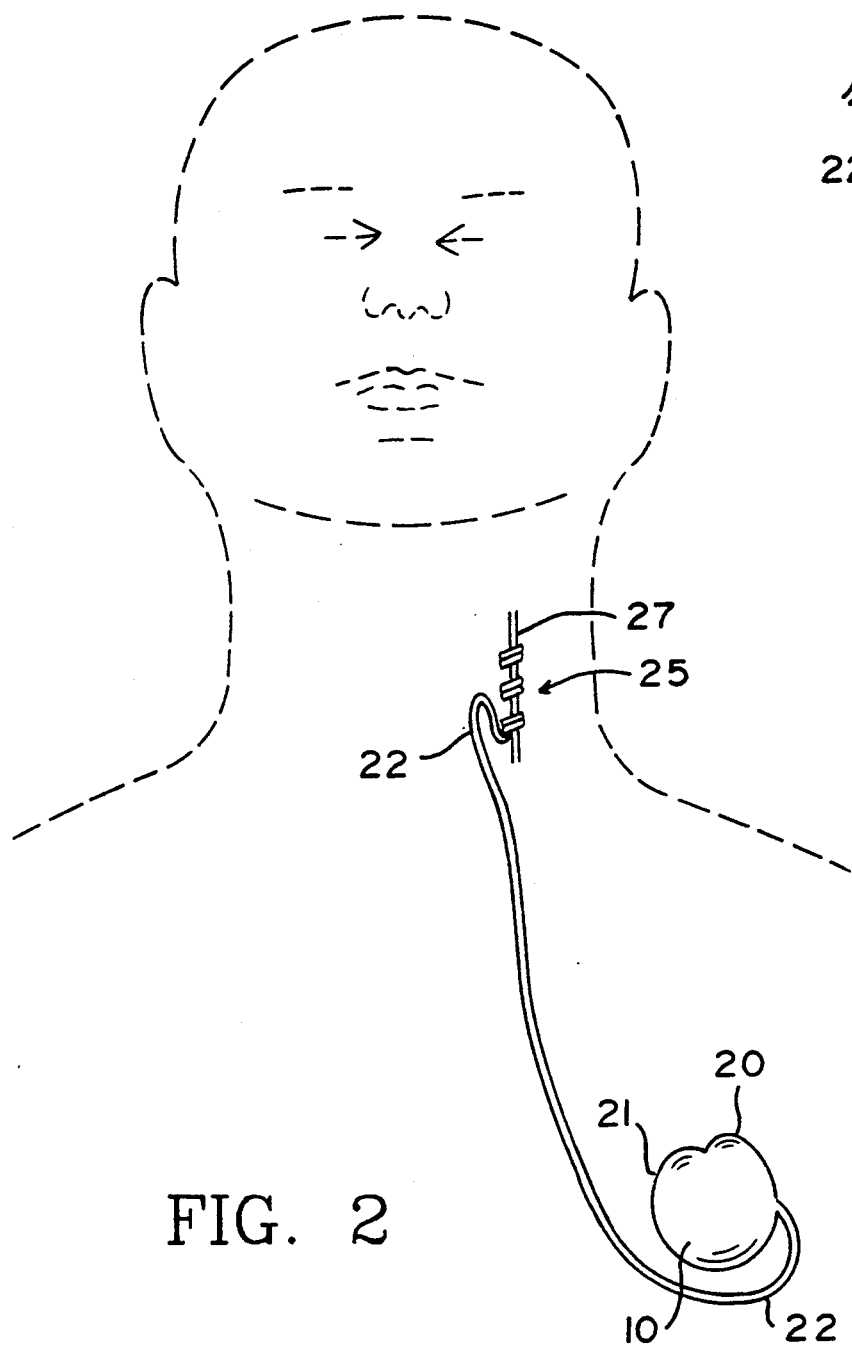
FIG. 2 is a simplified fragmentary illustration of a preferred embodiment of the stimulus generator and lead/electrode system of the neurostimulator implanted in the patient's body for stimulation of the vagus nerve at an exemplary site.
Figure 5:
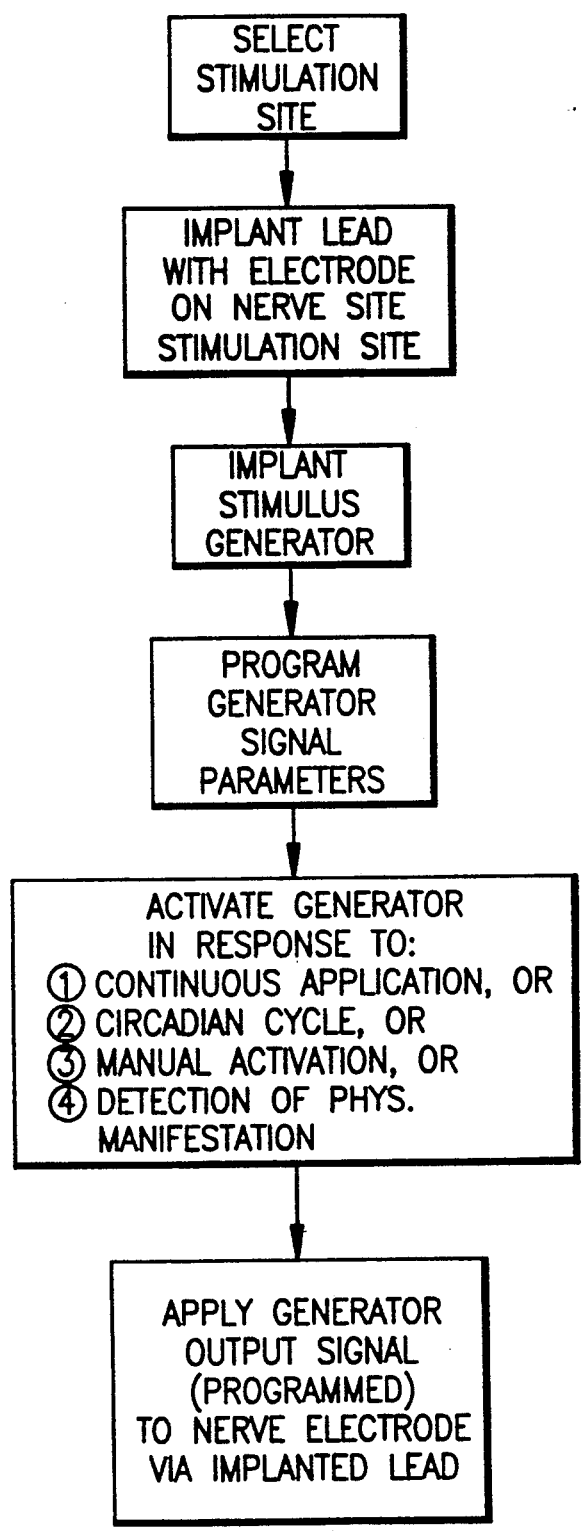
FIG. 5 is a flowchart of the method of the present invention.

The stimulus generator 10 (FIG. 1) of the neurostimulator is preferably adapted to be implantable in the patient's body, in a pocket formed by a surgical incision just below the skin in the chest as shown in FIG. 2. The overall neurostimulator includes implantable stimulating electrodes (described below) together with a lead system 22 for applying the output signal (electrical stimuli) of the stimulus generator to the patient's vagus nerve. Components external to the patient's body include a programming wand for telemetry of parameter changes to the stimulus generator and monitoring signals from the generator, and a computer and associated software for adjustment of parameters and control of communication between the generator, the programming wand and the computer. These external components of the system are not shown in the drawings.

As shown in FIG. 1, stimulus generator 10 includes a battery (or set of batteries) 12, which may be of any reliable long-lasting type conventionally employed for powering implantable medical electronic devices, such as a single lithium thionyl chloride cell. The terminals of cell 12 are connected to the input terminals of a voltage regulator 13, which is used to smooth the battery output to produce a clean, steady output voltage, and for enhancement thereof such as voltage multiplication or division if necessary for a specific application.

Regulator 13 supplies power to logic and control section 15, which includes a microprocessor (not shown) and controls the programmable functions of the device. Among these programmable functions are the parameters of the pulse sequences delivered by the generator, including, for example, output current or voltage, output signal frequency, output signal pulse width, output signal on-time, output signal off-time, daily treatment time for continuous or periodic modulation of vagal activity, and output signal-start delay time. Such programmability allows the output signal of the generator to be selectively tailored for application to the stimulating electrode assembly or array 25 (FIGS. 2 and 3) to obtain the desired modulation of the electrical activity of the vagus nerve for treating (suppressing) the chronic pain. Timing signals for the logic and control functions of the generator are provided by a crystal oscillator 16.

The stimulus generator programming may be set to provide automatic activation of the generator continuously, periodically or even intermittently. A magnetically-actuated reed switch 14, for example, is incorporated in the electronics package to provide the generator with the capability for manual activation by the patient (by use of an external magnet, not shown, placed immediately adjacent to the package or its implant site). Other patient activation techniques, such those described in copending U.S. application Ser. No. 07/793,842, filed Nov. 18, 1991 in the names of Ross G. Baker, Jr. et al. ("the '842 application"), assigned to the same assignee as the instant application, may alternatively be employed to allow patient activation of the neurostimulator.

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician or subordinate technician) by means of the external computer and the programming wand.

Logic and control section 15 of the stimulus generator 10 also controls an output circuit 19 which generates the programmed signal levels appropriate to the nature of the pain being treated. The programmed output signal of circuit 19 is delivered to an electrical connector 20 on the housing 21 of the generator and to lead assembly 22 connected to the stimulating electrodes (FIGS. 2 and 3). The parameters of the stimulating signal of the implanted device may be calibrated by telemetry (via the programming wand) according to the needs of the particular patient and the results then programmed into the microprocessor for delivery of the pain treatment upon activation of generator 10.

Housing 21 in which stimulus generator 10 is encased is hermetically sealed and composed of a material such as titanium which is biologically compatible with the fluids and tissue of the patient's body. Further details of suitable structure and operation of the neurostimulator, beyond those by which the device is adapted to treat pain as described herein, are available in the '172 patent, to which the reader is referred.

FIG. 2 illustrates the preferred location of implanted generator 10, in case 21 with connector 20, in the patient's chest. A stimulating nerve electrode assembly 25 (FIG. 3) is conductively connected to the distal end of insulated electrically conductive lead 22 which is attached at its proximal end to connector 20. Electrode assembly 25 includes a bipolar stimulating electrode, preferably of the type described in U.S. Pat. No. 4,573,481 to Bullara. The electrode assembly is surgically implanted on the vagus nerve 27, preferably in the cervical region, but as noted earlier herein, the site of the vagal stimulation may generally be at any point above the locality of the pain being experienced by the patient and which is to be suppressed as a result of the stimulation. The two electrodes 25-1 and 25-2 are wrapped about the vagus nerve, and the assembly is secured to the nerve by a spiral anchoring tether 28 preferably as disclosed in U.S. Pat. No. 4,979,511 to Reese S. Terry, Jr. and assigned to the same assignee as the instant application. Lead(s) 22 is secured, while retaining the ability to flex with movement of the chest and neck, for example, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve), for an electrode assembly to be implanted on the vagus nerve at the site shown in FIG. 2. Specific dimensions of the assembly will depend on the specific site of the implant.

The stimulus generator may be programmed with an IBM-compatible personal computer (PC, not shown) using programming software of the type copyrighted and registered by Cyberonics, Inc., the assignee of the instant application, with the Register of Copyrights, Library of Congress, or other suitable software based on the description herein, and a programming wand (not shown). The wand and software permit noninvasive communication with the generator after the latter is implanted.

Figure 4:
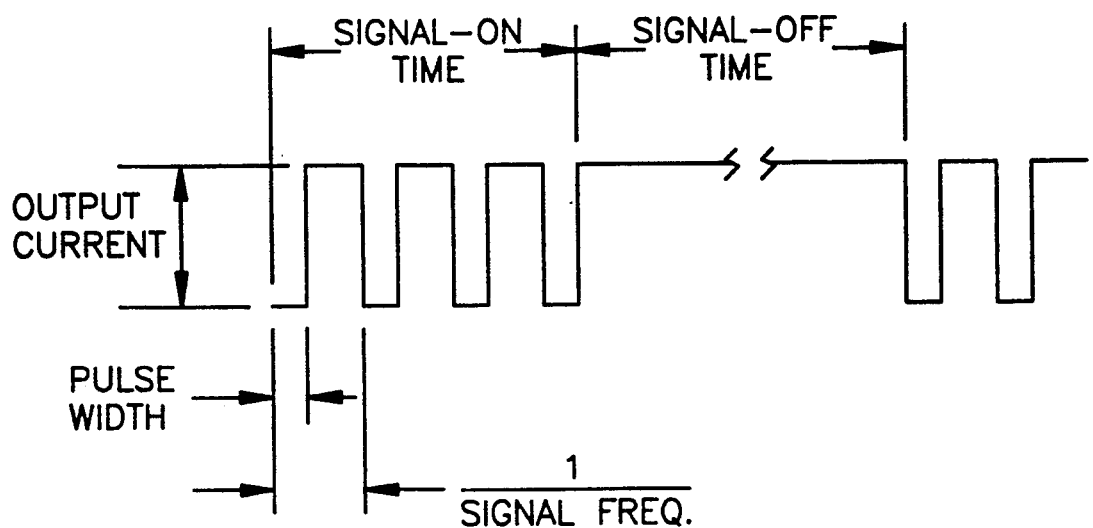
FIG. 4 is an illustrative idealized electrical output signal waveform of the stimulus generator useful for clarifying relevant parameters of the signal developed by the stimulus generator for application to the nerve, and for explaining the operation of the device.

The operation of stimulus generator 10 to control and treat the chronic or persistent pain will be described with reference to FIG. 4, which illustrates the general nature, in idealized representation, of the output signal waveform delivered by output section 19 of the neurostimulator to electrode assembly 25. This illustration is presented principally for the sake of clarifying terminology, including the parameters of output signal on-time, output signal off-time, output signal frequency, output signal pulse width, and output signal current.

A suitable general range of stimulation parameters for selection depending on the needs of the individual patient, and a more specific range of typical values of each parameter of the stimulating output signal for treating and controlling pain are set forth in the following Table:

TABLE

|  | General (Range) | Typical (Range) |
|---|---|---|
| Pulse Width | 0.5–2.0 ms | 0.5–2.0 ms |
| Output Current | 0.1–10.0 mA | 0.5–3.0 mA |
| Frequency | 5–100 Hz | 10–40 Hz |
| ON Time | 5–60 sec | 5–60 sec |
| OFF Time | 5 sec–1 hr | 5–20 min |
| Frequency sweep (optional) |  | 10–50 Hz |
| Random frequency (optional) |  | 10–50 Hz |

Preferably, the neurostimulator is programmed to be activated automatically and periodically for predetermined intervals throughout each day. That is, the stimulator is operated continuously so that it generates, for example, electrical output pulses of 2.0 ms width at a repetition frequency of 30 Hz with an output current of 1.4 milliamperes for an ON time duration of seven seconds. At the conclusion of each ON time interval, the stimulator becomes inactive for an OFF time period of, say, two minutes, after which it is again activated to generate pulses according to the programmed settings for the programmed ON time interval. Alternatively, in cases where the intensity of the pain is not sufficiently severe to interfere with or interrupt patient sleep, the automatic cycle of periodic activation for the programmed alternating ON time-OFF time may be set to occur only during the hours that the patient is normally awake, with a suitable overlap into the normal sleep hours, according to his or her circadian cycle.

In suitable cases, the programmed stimulation strategy may be implemented so that the device may be manually triggered into activation by the patient when pain is sensed, using, for example, the external magnet or one of the other patient activation techniques described in the '842 application. In all such cases, however, the stimulator is pre-programmed by the attending physician in an override mode to automatically cease operation after expiration of a prescribed period determined according to the nature and pattern of the pain experienced by the particular patient. The stimulus generator may be reactivated by the patient when the pain returns. The patient activation capability may be provided as an alternative to either of the automatic activation programs described above (continuous or awake period), or may be made available as a supplement to the awake period program so that the patient can alleviate pain which disturbs sleep.

Another but less desirable alternative or adjunct to the stimulator activation programs is to trigger the activation automatically in response to the sensing of a typical physical manifestation of the patient in reaction to pain, where applicable, such as the detection of severe muscular contractions in a selected region affected by the pain, by an implanted electrical impedance sensor 36 (FIG. 2) of any known type which is connected to the stimulus generator 10 via a separate lead 37 and connector 20. Because pain is subjective, the preferred control mode for activation of the stimulus generator is manually by the patient, in a manner such as that described above. The problem with using a feedback signal of some type to trigger activation of the stimulus is that the feedback signal must be derived from a specific mechanism attributable to pain, and must be a reliable indicator.

As has been discussed earlier herein, the desire is to excite (or modulate the electrical activity of) the afferent small fibers of the vagus nerve by suitable electrical stimulation of the nerve at a site preferably above the location of the pain sensed by the patient, to activate a descending anti-nociceptive pain pathway (nerve fiber tract) and thereby inhibit the incoming pain signals to the brain (the recognition or perception of pain in the thalamus) and the sensation of pain by the patient. Of course, there are limitations on the vagal stimulation site relative to the location of the pain—one example being the existence of chronic headache or facial pain—in which case the electrode array may be implanted at a site lower than that of the pain, e.g., in the patient's neck for this example, albeit perhaps (but not necessarily) less effective in inhibiting the pain.

It is noteworthy that the visceral afferents carried by the vagus nerve, and particularly the small C fibers, usually are not interpreted at a conscious level. For example, an individual usually does not experience the stretch of the aorta, but such a stretch activates vagal reflexes. Although vagal afferents are not truly nociceptive from that standpoint, vagal afferent stimulation according to the invention activates a descending anti-nociceptive pathway. The same pathway may be activated by many other inputs, primarily central inputs rather than peripheral inputs.

The selection of patients suffering chronic or persistent pain as candidates for the use of a neurostimulator and the treatment regimen described herein would be based, at least in substantial part, on the following criteria. The pain should be chronic or persistent and diagnosed, after appropriate examination and tests have been performed, as neuropathic or psychogenic. Patients experiencing chronic nociceptive pain should be considered candidates only if suffering a disease diagnosed as terminal. The patient should have the physical and psychological characteristics appropriate to tolerate implantation of the neurostimulator (including absence of contraindications and debilitating side effects). Contraindications would likely include cardiac disease and gastric ulcers. Preferably, the pain should be intractable to drug therapy (including the existence of contraindications or side effects which tend to outweigh any potential relief). Finally, the pain suffered by the particular patient should be found to respond to (i.e., be fully or satisfactorily at least partially relieved by) the vagal stimulation by tests conducted before a permanent implant is performed.

For the latter purpose, an external stimulus generator may be employed with leads extending percutaneously to the implanted nerve electrode assembly. The most serious problem encountered with such a temporary arrangement is the potential for infection, but that risk can be suitably minimized to justify the relatively short term tests required to determine whether the pain suffered by the patient under observation is sufficiently relieved to characterize the neurostimulation of the present invention as successful treatment. If it is, a permanent implant may be performed.

Various features may be incorporated into the neurostimulator for purposes of the safety and comfort of the patient. For example, comfort would be enhanced by programming the electrical stimulus delivered to the electrodes to ramp up during the first two seconds of stimulation, rather than to be delivered abruptly. Also, the implanted generator should be provided with a clamping circuit to limit the voltage delivered to the vagus nerve to a maximum level which is sufficient to produce the desired result without exceeding the patient's tolerance or the potential for vagus nerve damage.

The programmable functions and capabilities of the neurostimulator are designed and implemented to permit noninvasive communication with the stimulus generator after it is implanted, which is useful for both activation and monitoring functions. Beyond the essential functions of the device, the programming software may readily be structured to provide straightforward menu-driven operation, HELP functions, prompts, and messages to facilitate simple and rapid programming while keeping the programmer (the physician or a technician working under the physician's direction) fully informed of everything occurring at each step of a sequence. Programming capabilities should include capability to selectively modify the variable parameters of the stimulus generator and its output signal, to test device diagnostics, and to store and retrieve telemetered data. It is desirable that when the implanted unit is interrogated, the present state of the adjustable parameters be displayed on the monitor of the external PC. The programmer may then conveniently change any or all of those parameters at the same time, and, if a particular parameter is selected for change, all permissible values for that parameter may be displayed so that the programmer may select an appropriate desired value for entry into the neurostimulator.

Pre-implant diagnostics testing should be conducted to verify proper operation of the device, and to detect the existence of problems such as with communication, the battery, or the lead/electrode impedance. A low battery reading, for example, would be indicative of imminent end of life of the battery and need for implantation of a new device. The nerve electrode assembly is capable of indefinite use absent observation of a fault or failure during the diagnostics testing.

Although a preferred embodiment and method of treating and controlling pain according to the invention have been described herein, it will be apparent to those skilled in the art from a consideration of the foregoing description that variations and modifications of the disclosed embodiments, methods and techniques may be made without departing from the true spirit and scope of the invention. For example, although a totally implantable device is preferred, the electronic energization package may, if desired, be located primarily external to the body. Stimulation can be achieved with an RF power device implemented to provide the necessary energy level. The implanted components may be limited to the lead/electrode assembly, a coil and a DC rectifier. Pulses programmed with the desired parameters would be transmitted through the skin with an RF carrier, and the signal thereafter rectified to regenerate a pulsed signal for application as the stimulus to the vagus nerve to modulate vagal activity. This would virtually eliminate the need for battery changes. The disadvantages of such an implementation are that the external transmitter must be carried by the patient, greater power is required for activation, and the output current to the nerve is less stable.

Accordingly, it is intended that the invention shall be limited only to the extent required by the appended claims and the rules and principles of applicable law.

What is claimed is:

1. A method of treating patients suffering from chronic or persistent pain which is neuropathic or psychogenic, or which is nociceptive in the case of a patient with terminal disease, the method including the steps of:
   implanting a nerve electrode assembly at a distal end of an electrical lead on the vagus nerve of the patient,
   implanting a stimulus generator in the patient's body for generating an output signal with variable electrical waveform parameters programmable externally of the body, and electrically connecting the generator to a proximal end of the lead internally of the patient to enable the generator, when activated, to selectively deliver a programmed electrical signal having predetermined electrical waveform parameters as a stimulus directly to the patient's vagus nerve via the implanted nerve electrode assembly for modulating electrical activity of the nerve to stimulate afferent fibers thereof and alleviate the pain under treatment, and
   selectively activating the generator to alleviate the pain under treatment.

2. The method of claim 1, including programming the electrical signal for selective stimulation of afferent fibers to activate a descending anti-nociceptive pathway to inhibit incoming pain signals to the brain.

3. The method of claim 2, including selectively applying the programmed electrical signal via said electrode assembly on the patient's vagus nerve at a stimulation site above the patient's sensed location of the pain to enhance inhibition of the pain signals.

4. The method of claim 3,
   including selecting the stimulation site for implantation of the electrode assembly to be on the cervical vagus nerve.

5. The method of claim 3, including
   delivering a pulse waveform having predetermined waveform parameters as the programmed electrical signal.

6. The method of claim 5, including
   implementing the stimulus generator so that the programmable waveform parameters of the pulse waveform include pulse width, output current, output voltage, pulse frequency, and on time and off time durations of the waveform.

7. The method of claim 3, including
   selectively applying the programmed electrical to the implanted electrode assembly on a continuous basis.

8. The method of claim 7, including
   intermittently interrupting application of the programmed electrical signal to the implanted electrode assembly.

9. The method of claim 3, including
   selectively applying the programmed electrical signal to the implanted electrode assembly substantially only during the period that the patient is normally awake according to the patient's circadian cycle.

10. The method of claim 3, including
    selectively applying the programmed electrical signal to the implanted electrode assembly automatically in response to detecting a physical manifestation of the pain.

11. The method of claim 3, including
    providing a means for manual initiation of application of the programmed electrical signal to the implanted electrode assembly by the patient.

12. A method for use in advancing the relief and control of pain, which comprises:
    providing an electrical lead having a proximal end and a distal end, with a stimulating electrode assembly at its distal end for implantation on a patient's vagus nerve,
    providing a stimulus generator for generating electrical pulse sequences with programmable values of electrical waveform parameters for selective application to the lead/electrode assembly when implanted on the vagus nerve,
    incorporating an electrical connector in the stimulus generator to accommodate the proximal end of the electrical lead,
    restricting the programmable ranges of values of the electrical waveform parameters of the electrical pulse sequences to values which in combination will stimulate the small afferent fibers of the vagus nerve when one or more programmed pulse sequences are applied directly to the nerve via the lead/electrode assembly, to activate a descending anti-nociceptive pathway and inhibit incoming pain signals,
    restricting the stimulus generator to physician selection of the control of commencement and cessation of the programmed pulse sequences to be applied to the lead/electrode assembly, and
    employing the stimulus generator together with the lead/electrode assembly for the relief and control of pain in sufferers of chronic pain.

13. The method of claim 12, including implementing the stimulus generator to make the electrical waveform parameters with programmable values include pulse width, amplitude and frequency, sequence duration and intervals.

14. A neurostimulator for treating persistent pain in human patients, comprising:
    stimulus generator means structured to be implantable in the patient's body and responsive to being energized for generating an electrical output waveform having programmable electrical parameter values,
    lead/electrode means electrically connectable at a proximal end to said stimulus generator means and structured to be implantable in the patient's body to be mounted at a distal end on the patient's vagus nerve for delivering the electrical output waveform of the stimulus generator means to a preselected site along the vagus nerve, programming means for tailoring the electrical output waveform of said stimulus generator means with electrical parameter values in a respective preset range of values of each parameter, the electrical parameter values of the electrical output waveform being selected to produce stimulation of the afferent fibers of the vagus nerve to activate a descending anti-nociceptive pathway of the nerve to block incoming pain signals, and means for energizing said stimulus generator means to generate its electrical output waveform with pre-programmed electrical parameter values in each respective preset range selected to block incoming pain signals over predetermined intervals when pain is experienced.

15. The neurostimulator of claim 14, wherein
said electrical output waveform is a pulse waveform, and
said programming means allows selection of the electrical parameter values of the pulse waveform from among the respective preset range of values for each parameter, including at least the parameters of pulse width, pulse current level, pulse frequency, and on time and off time durations of the pulse waveform.

16. The neurostimulator of claim 15, wherein
said means for energizing said stimulus generator means includes at least one activating means selected from the group consisting of means for manual activation of the stimulus generator means by the patient, means for automatic activation of the stimulus generator means in response to detection of a physical manifestation of reaction by the patient to the onset of pain, means for automatic activation of the stimulus generator means to continuously generate the pulse waveform for periodic intervals of time determined by the selected values of on time and off time durations of the pulse waveform, and means for automatic activation of the stimulus generator means substantially only during a predetermined normal awake period for the patient according to the patient's circadian cycle.

* * * * *